US010918718B2

(12) United States Patent
Mo et al.

(10) Patent No.: US 10,918,718 B2
(45) Date of Patent: Feb. 16, 2021

(54) SONOSENSITIVE THERAPEUTIC OR DIAGNOSTIC AGENT

(71) Applicant: Oxsonics Limited, Oxford (GB)

(72) Inventors: Steven Mo, Oxford (GB); Robert Crispin Carlisle, Oxford (GB); Leonard W. Seymour, Oxford (GB); Constantin-Cassios Coussios, Oxford (GB)

(73) Assignee: Oxsonics Limited, Oxford (GB)

( * ) Notice: Subject to any disclaimer, the term of this patent is extended or adjusted under 35 U.S.C. 154(b) by 721 days.

(21) Appl. No.: 15/031,199

(22) PCT Filed: Oct. 21, 2014

(86) PCT No.: PCT/GB2014/053135

§ 371 (c)(1),
(2) Date: Apr. 21, 2016

(87) PCT Pub. No.: WO2015/059460

PCT Pub. Date: Apr. 30, 2015

(65) Prior Publication Data

US 2016/0263222 A1 Sep. 15, 2016

(30) Foreign Application Priority Data

Oct. 22, 2013 (GB) .................................. 1318668.9

(51) Int. Cl.

| | |
|---|---|
| ***A61K 9/50*** | (2006.01) |
| ***A61K 41/00*** | (2020.01) |
| ***A61K 47/69*** | (2017.01) |
| ***A61K 47/60*** | (2017.01) |
| ***A61K 33/24*** | (2019.01) |
| ***A61M 37/00*** | (2006.01) |

(52) U.S. Cl.

CPC .......... *A61K 41/0047* (2013.01); *A61K 33/24* (2013.01); *A61K 41/0028* (2013.01); *A61K 47/60* (2017.08); *A61K 47/6923* (2017.08); *A61K 47/6929* (2017.08); *A61M 37/0092* (2013.01); *A61M 2037/0007* (2013.01)

(58) Field of Classification Search

CPC ...... A61K 8/8152; A61K 9/50; A61K 9/5005; A61K 9/501; A61K 9/5026; A61K 9/5031; A61K 9/5078; A61L 29/085; A61L 29/08; A61B 2017/22089; A61B 2017/22091

See application file for complete search history.

(56) References Cited

U.S. PATENT DOCUMENTS

| | | | | |
|---|---|---|---|---|
| 2006/0275371 A1 | 12/2006 | Dai et al. | | |
| 2007/0071683 A1* | 3/2007 | Dayton | ................ A61K 31/337 | 424/9.5 |
| 2008/0045865 A1* | 2/2008 | Kislev | .................... A61B 5/411 | 601/3 |
| 2008/0160090 A1* | 7/2008 | Oraevsky et al. | ............ 424/489 | |
| 2008/0237028 A1* | 10/2008 | Kislev | .................... A61B 8/481 | 204/157.15 |
| 2008/0312581 A1* | 12/2008 | Hardy | ............................. 604/22 | |
| 2011/0014297 A1 | 1/2011 | Lee et al. | | |
| 2011/0044903 A1* | 2/2011 | Borrelli | ................ A61K 49/223 | 424/9.1 |
| 2011/0059020 A1 | 3/2011 | Hirai et al. | | |
| 2012/0045397 A1 | 2/2012 | Liu | | |
| 2012/0095325 A1 | 4/2012 | Wei et al. | | |
| 2012/0164230 A1 | 6/2012 | Feazell et al. | | |
| 2012/0214218 A1 | 8/2012 | Xing et al. | | |
| 2013/0066190 A1 | 3/2013 | Peyman | | |
| 2013/0261442 A1 | 10/2013 | Yang | | |
| 2016/0250352 A1 | 9/2016 | Mo et al. | | |

FOREIGN PATENT DOCUMENTS

| | | |
|---|---|---|
| JP | 2005/287507 A2 | 10/2005 |
| WO | 2008/101019 | 8/2008 |
| WO | 2009/039502 | 3/2009 |
| WO | 2010/048623 | 4/2010 |
| WO | 2011/072133 | 6/2011 |
| WO | 2012/039979 | 3/2012 |
| WO | 2012/066334 | 5/2012 |

OTHER PUBLICATIONS

Anderson et al (Invest Radiol Oct. 2010; 45 (1): 579-585) (Year: 2010).*

International Search Report corresponding to PCT/GB2014/053134 dated Dec. 19, 2014; 4 pages.

International Search Report corresponding to PCT/GB2014/053135 dated Feb. 13, 2015; 5 pages.

Delogu et al.; Functionalized multiwalled carbon nanotubes as ultrasound contrast agents; Proceedings of the National Academy of Sciences, Oct. 9, 2012; vol. 109, Nr:41, pp. 16612-16617.

Diaz Roberto J et al.; ET-37; Targeted delivery of gold nanoparticles to the invasive front of malignant glioma using transcranial magnetic resonance image guided focused ultrasound; Neuro-Oncology; 16th Annual Scientific Meeting of the Society for Neuro-Oncology in Conjunction with the AANS/CNS Section on Tumors, Nov. 2011; Nov. 17, 2011-Nov. 20, 2011, vol. 13, Nr:Suppl. 3, pp. iii115, abstract.

*Primary Examiner* — Micah Paul Young

(74) *Attorney, Agent, or Firm* — Kilpatrick Townsend & Stockton LLP

(57) ABSTRACT

The invention disclosed herein relates to a method of cavitation-induced delivery of a therapeutic or diagnostic agent to a human or animal subject. In particular the invention provides an agent for use in a method of diagnosis or treatment of a human or animal subject, the method comprising exposing the subject to ultrasound, wherein the agent comprises a therapeutic or diagnostic component which is covalently bound to a dense component, the dense component having a density greater than that of the therapeutic or diagnostic component, and wherein either the dense component is a cavitation initiator or the method comprises administering to the subject a further agent which is a cavitation initiator. Binding of the dense component enhances cavitation-induced transport of the therapeutic or diagnostic component.

17 Claims, 10 Drawing Sheets

(56) References Cited

OTHER PUBLICATIONS

Gu et al.; Gold-doxorubicin nanoconjugates for overcoming multidrug resistance; Nanomedicine: Nanotechnology, Biology and Medicine; vol. 8, 2012, pp. 204-211.
Kievit et al.; Doxorubicin loaded iron oxide nanoparticles overcome multidrug resistance in cancer in vitro; Journal of Controlled Release; vol. 152, 2011, pp. 76-83.
Liu and Thierry; A solution to the PEG dilemma: efficient bioconjugation of large gold nanoparticles for biodiagnostic application using mixed layers; Langmuire, vol. 28, 2012, pp. 15634-15642.
Liu et al.; Synthesis, stability and cellular internalization of gold nanoparticles containing mixed peptide-poly(ethylene glycol) monolayers; Analytical Chemistry, vol. 79, No. 6, 2007, pp. 2221-2229.
Messerschmidt Sylvia K E; et al.; Targeted lipid-coated nanoparticles: Delivery of tumor necrosis factor-functionalized particles to tumor cells; Journal of Controlled Release, Jul. 1, 2009; vol. 137, Nr:1, pp. 69-77.
Mo et al.; A New Gold-Nanoparticle-Based Coating to Enhance Ultrasound-Mediated Delivery of Nanomedicines to Tumours; 14th Int. Symposium on Therapeutic Ultrasound, Apr. 2, 2014, 1 page.
Mo et al.; Coating of adenovirus type 5 with cleavable PEGylated gold nanoparticles for enhanced protection and circulation; Human Gene Therapy, May 1, 2013; vol. 24, Nr:5, pp. A13(S8.4).
Mo et al.; Goldnanoparticles for the enhancement of adenovirus stealthing; Human Gene Therapy, 2013; vol. 24, Nr: 12, pp. A67-A68.
Mo et al.; Ultrasound-enhanced drug delivery for cancer; Expert Opinion on Drug Delivery, Dec. 1, 2012; vol. 9, Nr:12, pp. 1525-1538.
Mo, Steven; ORA Thesis: Cavitation-enhanced tumour-targeting virotherapy by ultrasound, 2013.
Soliman, Mahmoud et al.; Multicomponent Synthetic Polymers with Viral-Mimetic Chemistry for Nucleic Acid Delivery; Molecular Pharmaceutics, Jan. 1, 2012; vol. 9, Nr:1, pp. 1-13.
Tsai et al.; Tumor necrosis factor ineraction with gold nanoparticles; Nanoscale, vol. 4, No. 10, 2012, pp. 3208-3217.
Vigderman Leonid; Zubarev Eugene R; Therapeutic platforms based on gold nanoparticles and their covalent conjugates with drug molecules; Advanced Drug Delivery Reviews, May 18, 2012; vol. 65, Nr:5, pp. 663-676.
Visaria et al.; Enhancement of tumor thermal therapy using gold nanoparticle assisted tumor necrosis factor-alpha delivery; Molecular Cancer Therapeutics; vol. 5, 2006, pp. 1014-1020.
Wang et al.; Au-nanoparticle coated mesoporous silica nanocapsule-based multifunctional platform for ultrasound mediated imaging, cytoclasis and tumor ablation; Biomaterials, vol. 34(8), 2013, pp. 2057-2068.
Wang, Xiufang et al.; Assembly of dandelion-like Au/PANI nanocomposites and their application as SERS nanosensors; Biosensors and Bioelectronics, Feb. 1, 2011; vol. 26, Nr:6, pp. 3063-3067.
Kim et al., "Enhancing the therapeutic efficacy of adenovirus in combination with biomaterials," Biomaterials Feb. 2012; 33(6): 1838-1850.
De Paula et al., "Hydrophobization and bioconjugation for enhanced siRNA delivery and targeting," RNA 2007; 13:431-456.

* cited by examiner

SONOSENSITIVE THERAPEUTIC OR DIAGNOSTIC AGENT

CROSS-REFERENCE TO RELATED APPLICATIONS

This application is a national phase application under 35 U.S.C. 371 claiming priority to PCT/GB2014/053135, filed Oct. 21, 2014, which application claims priority to GB 1318668.9, filed Oct. 22, 2013, the teachings of which are hereby incorporated by reference in their entireties for all purposes.

FIELD OF THE INVENTION

The invention disclosed herein relates to a method of cavitation-induced delivery of a therapeutic or diagnostic agent to a human or animal subject, and in particular agents for use in methods involving ultrasound-induced cavitation.

BACKGROUND OF THE INVENTION

Therapeutic and diagnostic methods using ultrasound are known. In particular, it is known to use ultrasound to induce inertial cavitation in the body, whereby a void or bubble in the body expands and then rapidly collapses, causing broadband acoustic emissions, a shockwave and fluid microstreaming in the vicinity of the bubble. Microstreaming caused by cavitation can be used to deliver therapeutic agents to their biological targets in vivo, for example by extravasation of a therapeutic agent from the bloodstream into surrounding tissue.

However, in known methods, the pressure of ultrasound required to produce an inertial cavitation effect sufficient to deliver a therapeutic agent to its target is high, typically from 5 MPa to 10 MPa. Exposing a subject to high ultrasound pressures can have adverse effects and requires transducers that add significant cost to the procedure. There is therefore a trade off between the therapeutic benefit of ultrasound in delivery of a therapeutic agent, and the need to minimise the pressure of ultrasound used.

SUMMARY OF THE INVENTION

It has now been found that cavitation-induced delivery of a therapeutic or diagnostic agent can be enhanced by increasing the density of a therapeutic or diagnostic agent. That provides effective delivery under inertial cavitation, while minimising the pressure of ultrasound required. Thus, the present invention increases the response of a therapeutic or diagnostic agent to ultrasound-induced cavitation by providing a dense component attached to a therapeutic or diagnostic component, the dense component enhancing cavitation-mediated transport.

The present invention therefore provides an agent for use in a method of diagnosis or treatment of a human or animal subject, the method comprising exposing the subject to ultrasound, wherein the agent comprises a therapeutic or diagnostic component which is covalently bound to a dense component, typically a cavitation-enhancing dense component, the dense component having a density greater than that of the therapeutic or diagnostic component, and wherein either the dense component is a cavitation initiator or the method comprises administering to the subject a further agent which is a cavitation initiator.

In some embodiments of the present invention, a component is bound to the therapeutic or diagnostic component which is capable of acting as a cavitation initiator, and also has the effect of increasing the density of the agent.

In other embodiments of the present invention, a component is bound to the therapeutic or diagnostic component which has the effect of increasing the density of the agent, and a separate cavitation initiator not bound to the therapeutic agent is administered to the subject.

The present invention also provides a method of diagnosis or treatment of a human or animal subject, the method comprising administering to the subject an agent and exposing the subject to ultrasound, wherein the agent comprises a therapeutic or diagnostic component which is covalently bound to a dense component, typically a cavitation enhancing dense component, the dense component having a density greater than that of the therapeutic or diagnostic component, and wherein either the dense component is a cavitation initiator or the method comprises administering to the subject a further agent which is a cavitation initiator.

The present invention also provides use of an agent in the manufacture of a medicament for use in a method of treatment or diagnosis of a human or animal subject, the method comprising administering to the subject an agent and exposing the subject to ultrasound, wherein the agent comprises a therapeutic or diagnostic component which is covalently bound to a dense component, typically a cavitation enhancing dense component, the dense component having a density greater than that of the therapeutic or diagnostic component, and wherein either the dense component is a cavitation initiator or the method comprises administering to the subject a further agent which is a cavitation initiator.

BRIEF DESCRIPTION OF THE FIGURES

FIG. 4*a* shows biodistribution and FIG. 4*b* shows tumor accumulation at 30 min using QPCR, n=4, SD shown, ANOVA analysis used.

DETAILED DESCRIPTION

Figure 1A:
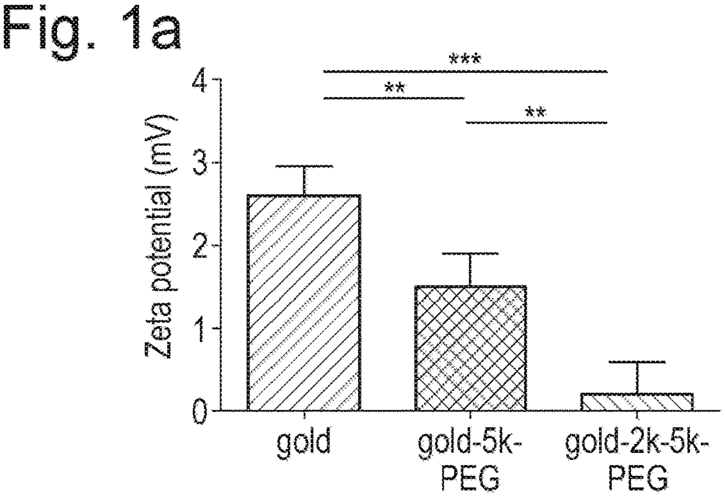
FIGS. 1*a* and 1*b* show zeta potential of each gold and Ad conjugation step was measured (n=5, SD shown); *, , and * represents p-value<0.05, 0.01, and 0.001, respectively.

In one aspect, the invention uses a therapeutic component. As used herein a therapeutic component is a substance having an effect which is desirable or beneficial as part of a method of treatment of the human or animal body by therapy. Therapeutic substances include, but are not limited to pharmaceutical drugs, peptides, proteins, vaccines, antibodies, aptamers, nucleic acids, DNA, RNA, antisense oligonucleotides, viruses (e.g Ad5), radiopharmaceuticals and bacteria.

In another aspect the invention uses a diagnostic component. As used herein a diagnostic component is a substance having an effect which is desirable or beneficial as part of a method of diagnosis carried out on the human or animal body. Diagnostic substances include contrast agents, magnetic nanoparticles, radioisotopes and quantum dots.

As used herein a cavitation initiator is a substance comprising one or more gas or vapour filled cavities or "bubbles".

As used herein the term "ultrasound pressure" or "ultrasound pressure amplitude" refers to the rarefactional pressure amplitude of an ultrasound wave.

As used herein, a "cavitation-enhancing" dense component is a component that enhances cavitation-mediated transport. Thus, by increasing the overall density of the therapeutic or diagnostic component to which it is bound, the dense component increases the extent to which the agent is moved, or transported, by cavitation effects occurring in the vicinity. Thus, transport of the therapeutic or diagnostic, for example into tissue from the vasculature, may be enhanced.

The dense component has a density which is greater than that of the therapeutic or diagnostic component, thereby forming an agent which has an overall effective density greater than if the therapeutic or diagnostic component were administered on its own. The density of the dense component is typically two times or more that of the therapeutic or diagnostic component, e.g 2.5 times or more, 3 times or more, 3.5 times or more, 4 times or more, 4.5 times or more, or 5 times or more.

The dense component typically has a density of 3 g/mL or more, e.g. 4 g/mL or more, 5 g/mL or more, 10 g/mL or more or 15 g/mL or more.

The overall effective density of the agent is typically 1.5 times or more that of the therapeutic or diagnostic component, e.g. 2 times or more, 2.5 times or more, 3 times or more, 3.5 times or more or 4 times or more.

The overall effective density of the agent is typically 1.5 g/mL or more, e.g. 1.75 g/mL or more, 2 g/mL or more, 2.25 g/mL or more, 3 g/mL or more, 3.25 g/mL or more, or 3.5 g/mL or more.

The dense component is covalently bound to the therapeutic or diagnostic component. The covalent linkage between the dense component and the therapeutic or diagnostic component may be a direct bond, or a covalently bound linker, e.g. a polymeric linker. Covalent bonding between the dense component and the therapeutic or diagnostic component provides greater stability of the agent, for example it is typically stable in the vasculature.

Preferably the dense component is cleavably bound to the therapeutic or diagnostic component. As used herein the terms "cleavable" and "cleavably" refer to a covalent linkage which is stable under certain conditions, e.g. stable when in the vasculature, but cleavable under certain other conditions. Covalent linkages may for example be cleavable under certain pH conditions, under reducing conditions or oxidising conditions, or in the presence of enzymes, e.g. when under conditions with elevated levels of organ-specific endopeptidases (e.g. matrix metalloproteinases (MMP2)). The cleavable linkage is typically designed to be cleaved under conditions present in the target of the agent, in order to present the free therapeutic or diagnostic substance. For example, if the target of the agent is tumour tissue where reducing conditions prevail, the cleavable moiety may be cleavable under reducing conditions.

The dense component is typically bound to the therapeutic or diagnostic component with one or more polymer chains. Suitable polymer chains are non-toxic and biocompatible, e.g a non-toxic, biocompatible hydrophilic polymer. Particular polymer chains include but are not limited to poly (alkylene oxide), e.g. PEG, and PHMPA. PEG is preferred. The molecular weight of the polymer chains binding the dense component to the therapeutic or diagnostic component will depend on the desired overall size of the agent, which will in turn depend on its target, but polymer chains binding the dense component to the therapeutic or diagnostic component typically have a molecular weight of from 4 to 30 kD, e.g. 4 to 6 kD or 4.5 kD to 5.5 kD.

When the dense component is cleavably bound to the therapeutic or diagnostic component, the polymer chain typically comprises a cleavable moiety. Known moieties which are cleavable under reducing conditions include moieties comprising a S—S bond, such as that achieved using the crosslinker N-succinimidyl-3-(2-pyridyldithio)propionate (SPDP). Other moieties which are cleavable under certain conditions including for example a pH below 7.365 or the presence of organ specific endopeptidases, are known in the art. For example, acid labile hydrazide bonds are cleavable under reduced pH conditions and peptide bonds may be cleaved by endopeptidases such as matrix metalloproteinase (MMP2) . A skilled person can therefore select an appropriate cleavable moiety for an agent designed to target tissue having for example oxidising conditions, basic conditions, acidic conditions, conditions with raised endopeptidase (e.g. MMP2) levels.

Methods for attaching a therapeutic or diagnostic component to a polymer chain comprising a cleavable moiety are also known in the art and include the use of bifunctional crosslinking agents such as SPDP which is comprised of a N-hydroxysuccinimide ester to provide reactivity to primary amine groups and a 2-pyridyldithio to provide reactivity to sulphydryl groups.

The overall size of the dense component, and the number of dense components present in the agent, will depend on the desired overall size of the agent, which will in turn depend on the target of the biologic therapeutic as discussed in more detail further below. The agent may, for example, comprise one or a plurality of dense components. In one embodiment, two or more dense components are present, for example 5 or more or 10 or more dense components. In some embodiments the number of dense components is from 1 to 10, e.g. 1 to 5 or 1 to 2. Such embodiments may be used for therapeutic or diagnostic components of small size, e.g. antibodies. However, in other embodiments the number of dense components may be 10 to 300, e.g. 50 to 200, e.g. 80 to 120. Such embodiments may be used for larger therapeutic or diagnostic components such as viruses.

The dense component is typically a nanoparticle. As used herein a nanoparticle is any nano-scale particle, typically from 1 to 1000 nanometres in size e.g. 1 to 500, 1 to 100 or 1 to 10 nanometres. A nanoparticle may be, for example, an agglomerate of smaller nanoparticles.

Particular nanoparticles include but are not limited to metals such as gold, magnetic particles such as iron oxide, quantum dots or ultrasound responsive carbon nanoparticles. In some embodiments, gold may be preferred for certain therapeutic purposes because of its low toxicity, biocompatibility, suitability for surface modification and high density. The high density of gold means that the density of agents having gold nanoparticles as the dense component can be particularly high, thereby providing particularly effective enhancement of sensitivity to cavitation.

In some embodiments cavitation initiating nanoparticles are preferred as the dense component. Using cavitation initiating nanoparticles as the dense component not only increases the density of the agent, but ensures that the cavitation initiator is in the same location as the therapeutic or diagnostic substance (co-location). Co-location of cavitation initiator and therapeutic or diagnostic substance enhances the effectiveness of the cavitation technique in delivery and transport of the therapeutic or diagnostic substance.

Methods of attaching the dense component to a polymer chain for attachment to the therapeutic or diagnostic component are known in the art and include, for example, carbodiimide (EDG) chemistry which is suitable for attaching PEG polymer chains to nanoparticles including gold. Polymer chains can also be attached to dense components such as nanoparticles using reactions between N-hydroxysuccinimide or thiazolidine-2-thione groups and amine groups or between maleimide and thiol groups.

In some embodiments, the cavitation initiator, either forming the dense component or provided as a further separate agent, is an agglomerate of carbon nanoparticles. Voids between carbon nanoparticles in the agglomerate act as bubbles when subjected to ultrasound, expanding and then rapidly collapsing. However, the bubbles in the agglomerate are not destroyed in the process. An agglomerate of carbon nanoparticles typically has an overall size of 10 to 400 nm, e.g 100-300 nm or about 200 nm.

Other suitable cavitation initiators either forming the dense component or provided as a further separate agent include known cavitation inducing nanoparticles, such as those described in Mo et al.; Expert Opin Drug Deliv; 2012; 9(12); 1525-38, the contents of which is hereby incorporated by reference, and nanoscale particles having spherical or part spherical surface features or surface depressions of from 5 to 50 nm in size as described in WO 2012/066334, the contents of which is hereby incorporated by reference.

In some embodiments the dense component has a plurality of polymer chains attached thereto. Polymer chains attached to the dense component in this way provide the therapeutic or diagnostic component with shielding from bloodstream components when in vivo, thereby prolonging the circulation of the agent and improving its pharmacokinetics. The plurality of polymer chains are typically as described above for the polymer chains attaching the dense component to the therapeutic or diagnostic component, except they are typically of lower molecular weight, e.g. from 1 kD to 3 kD and preferably from 1.5 kD to 2.5 kD.

In these embodiments, the dense component typically has a plurality of polymer chains each having a molecular weight MW1 bound thereto and one or more polymer chains having a molecular weight MW2 bound thereto, wherein MW2 is greater than MW1 and the number of polymer chains having molecular weight MW1 is greater than the number of chains having MW2. Thus, the dense component typically has a relatively high number of relatively short polymer chains attached thereto, and one or a relatively low number (e.g. 1, 2, 3, 4 or 5) of relatively long polymer chains attached thereto (via which the dense component may be bound to the therapeutic or diagnostic component). MW1 and MW2 may each independently represent a particular molecular weight, or may represent a distribution of molecular weights. Typically, MW1 is from 1 to 3 kD. Typically, MW2 is from 4 to 30 kD, e.g. 4 to 6 kD. Preferably, MW1 is from 1.5 kD to 2.5 kD. Preferably, MW2 is from 4.5 kD to 5.5 kD. In one embodiment, MW1 is 2 kD and MW2 is 5 kD.

In these embodiments up to 99%, e.g. 1% to 99% of the surface of the dense component is typically modified by attachment to a polymer chain. In some examples of these embodiments 50% to 99% of the surface of the dense component is modified by attachment to a polymer chain, e.g. 80% to 99%, 85% to 95%, 88% to 92% or about 90%.

The number of polymer chains attached to the dense component will depend on the size of the dense component and the surface available for modification. When the dense component is a nanoparticle of 1-10 nm in size, 100 to 500 polymer chains may typically be attached to the nanoparticle, e.g. 200 to 300 polymer chains.

As mentioned above, the overall size of the agent is dependent on the length (molecular weight) of the polymer chains used to bind the dense component to the therapeutic or diagnostic component, the number of dense components present in the agent, whether a plurality of polymer chains are attached to the or each dense component and if so how many, the size of the or each dense component, and the size of the therapeutic or diagnostic component itself. A skilled person, having in mind a particular biological target may have a desired size of an agent for a particular therapeutic diagnostic or purpose.

The overall size of an agent of the invention can be in the region of 100-1000 nm, e.g. 100-500 nm or 100-300 nm.

For example, if a skilled person intends to target a tumour, then a particular size of the agent may be desired in order to improve accumulation in tumour tissue by the enhanced permeability and retention (EPR) effect. Tumour tissues may contain neovasculature having abnormal form and architecture, leading to abnormal molecular and fluid transport dynamics. That can cause agents of around 100 to 500 nm, e.g. 100 to 300 nm in size to accumulate in tumour tissue much more than they do in normal tissues. Agent sizes of 100 to 500 nm, e.g. 100 to 300 nm may therefore be desired, in particular for use in methods of treating a tumour.

For example, if the therapeutic or diagnostic component is an Ad5 virus of around 140 nm in size, and the target is a tumour, then an overall size in the desired range, e.g 100 to 500 nm or around 300 nm can be achieved by attaching 80 to 120, e.g. about 100 dense components of 5-10 nm, e.g. about 7 nm in size, each having 400 to 600, e.g about 500 polymer chains of 1.5 kD to 2.5 kD, e.g. about 2 kD in size bound thereto, and 2 to 10 polymer chains of molecular weight 4 kD to 6 kD, e.g. about 5 kD binding the dense component to the therapeutic or diagnostic component.

The ultrasound used in the method is not particularly limited and any frequency in the range 0.5 MHz to 5.0 MHz can be used. Further, any pressure sufficient to give definite inertial cavitation can be used. When used in combination with the enhanced density agents of the present invention ultrasound pressure amplitudes from 0.5 MPa can give definite inertial cavitation. Ultrasound pressure amplitudes used are typically less than 5 MPa, e.g. 3 MPa or less.

The agents of the invention may be administered by any suitable route, depending on the nature of the nature of the method of treatment, e.g. orally (as syrups, tablets, capsules, lozenges, controlled-release preparations, fast-dissolving preparations, etc); topically (as creams, ointments, lotions, nasal sprays or aerosols, etc); by injection (subcutaneous, intradermic, intramuscular, intravenous, etc.), transdermally (e.g. by application of a patch, gel or implant) or by inhalation (as a dry powder, a solution, a dispersion, etc).

In embodiments where the cavitation initiator is administered as a separate agent, the two agents may be administered together in the same pharmaceutical composition or in different compositions intended for separate, simultaneous, concomitant or sequential administration by the same or a different route.

An amount of agent to be administered as part of a method of treatment or diagnosis will depend on, for example, the identity of the therapeutic or diagnostic component and can be determined by one of skill in the art. Thus, the dose of the agent of the invention will typically be equivalent to or less than the dose of the therapeutic or diagnostic component present in the agent if administered alone, i.e. the amount of therapeutic or diagnostic component present in the agent administered will typically be the same or less than the amount that would be administered if in free form. The dose of the agents of the invention may be less than the equivalent amount of free therapeutic or diagnostic component for example to compensate for the enhanced pharmacokinetics seen in the agents of the invention as described above, for example 95% or less, 85% or less, 80% or less, 75% or less, 70% or less, 65% or less, 60% or less, 55% or less, or 50% or less.

The amount of cavitation initiator administered can be any appropriate dose as can be determined by a skilled person.

EXAMPLES

The present invention is illustrated below by the following non-limiting examples. A skilled person will appreciate that although the concept of increasing density to enhance response to ultrasound induced cavitation is illustrated below using certain methods and materials, the principle can be generally applied based on the foregoing description and is limited only by the scope of the appended claims.

Preparation Example 1

Formulation and Analysis of Gold-PEG and Ad–Gold-PEG Agent

Carbodiimide (EDC) chemistry was used to attach 5 molecules of 5 kDa thiol-PEG of per gold nanoparticle to which a further 257 copies of 2 kDa PEG were added to form a PEGylated "dandelion-like" structure (gold-PEG). N-succinimidyl 3-(2-pyridyldithio)propionate (SPDP) was then used to achieve linkage of this highly stealthed construct to Ad via a single reduction-cleavable bond between a 5 kDa PEG and an amine groups on the surface of the Ad, to give Ad–gold-PEG.

Figure 1B:
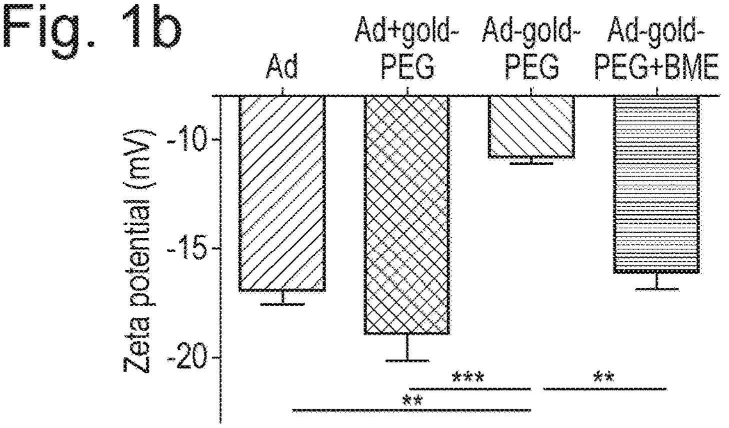
Figure 1C:
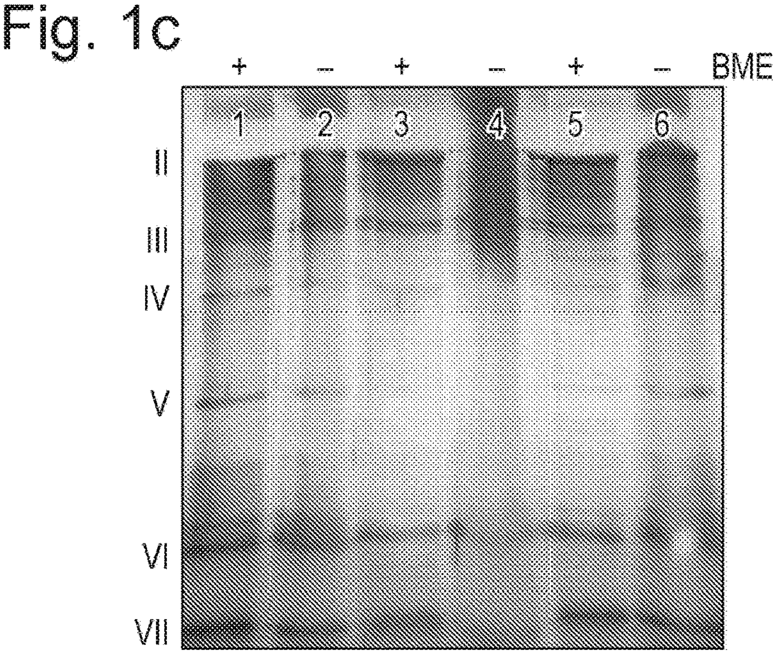
FIG. 1*c* shows gel electrophoresis showing reduction-reversible retarded migration of Ad proteins following conjugation to gold-PEG. SDS-PAGE silver staining was performed + or −'BME' reducing buffer (50 mM beta-mercaptoethanol), lanes 1 and 2=Ad, 3 and 4=Ad−gold-PEG, 5 and 6=Ad+gold-PEG. Roman numerals denote positions of Ad proteins according to molecular weight.
Figure 3B:
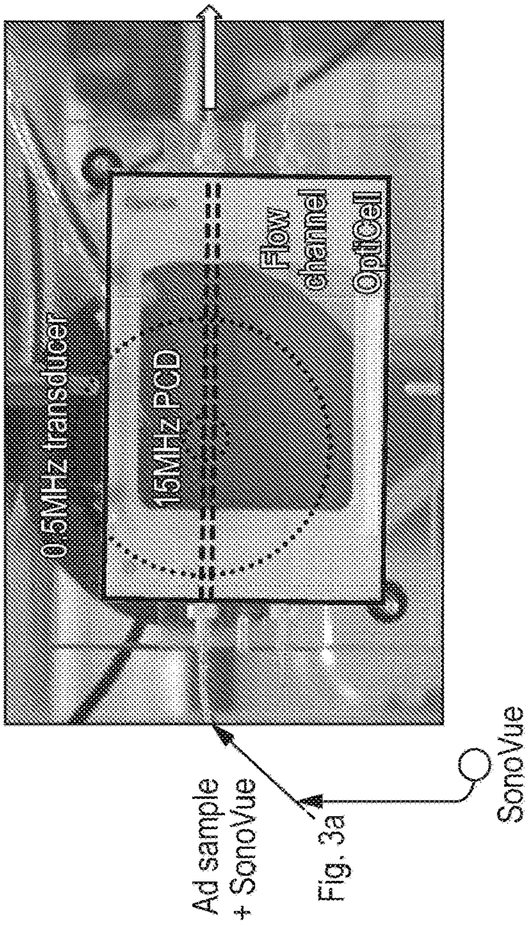
FIGS. 3*a* and *b* show in vitro ultrasound set-up
FIGS. 3*c-f* show influence of ultrasound exposure pressure on the penetration of Ad samples into TMM as assessed by QPCR. For each figure the left panel shows the number of Ad recovered at different depths from the vessel N=4, SD shown, ANOVA analysis and the right panel shows a representative frequency spectra detected over the course of the ultrasound exposure. Passive cavitation detection, shows increasing broadband acoustic emissions with increasing pressure of exposure, indicative of the occurrence of inertial cavitation.
FIG. 3*g* shows fluorescence microscopy analysis of green fluorescent protein transgene production from Ad or Ad-gold-PEG after ultrasound exposure at 180 or 1250 kPa, with or without BME treatment and 24 hours incubation. White dotted lines denote flow channel, as in FIG. 6*b*, and white arrows demarcate extent of infected region.
Figure 3A:
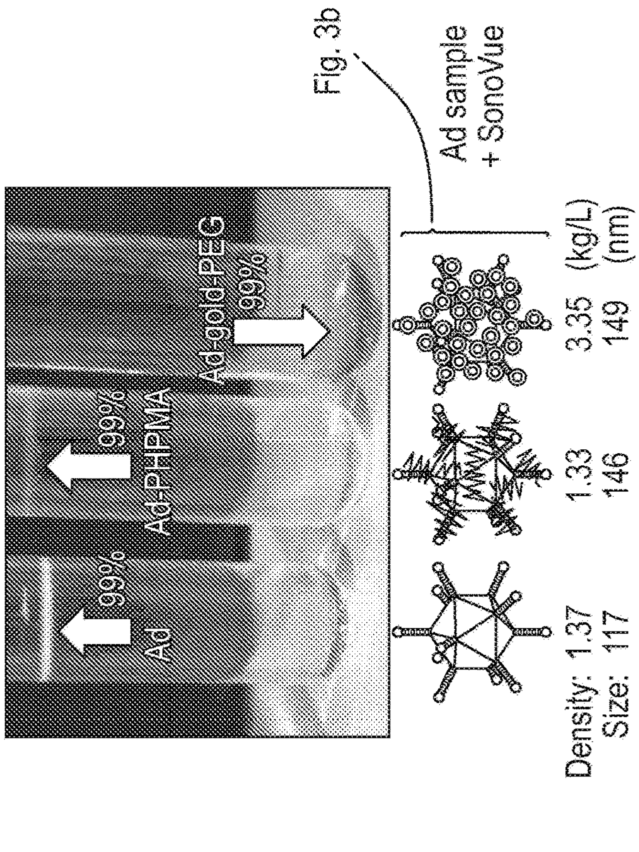
Figure 3C:
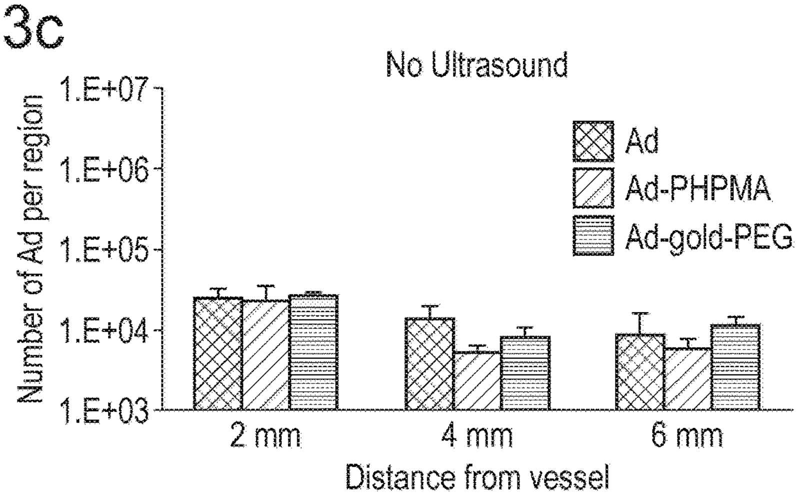
Figure 3D:
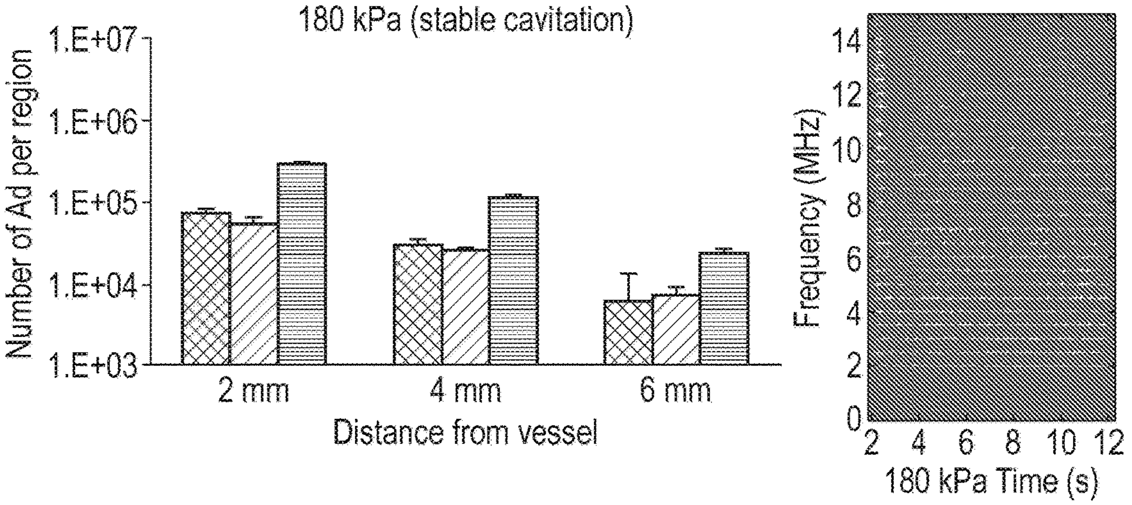
Figure 3E:
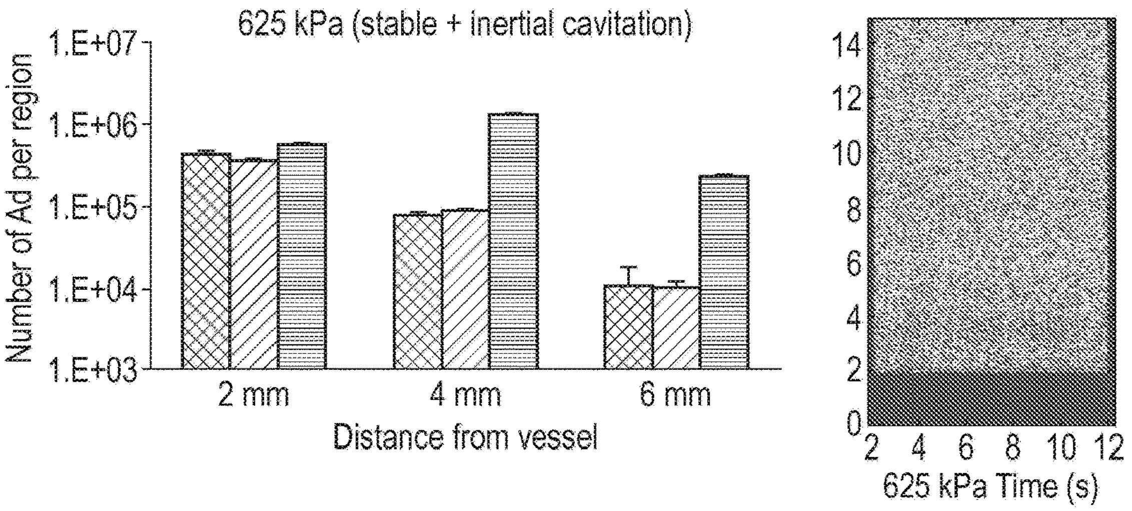
Figure 3F:
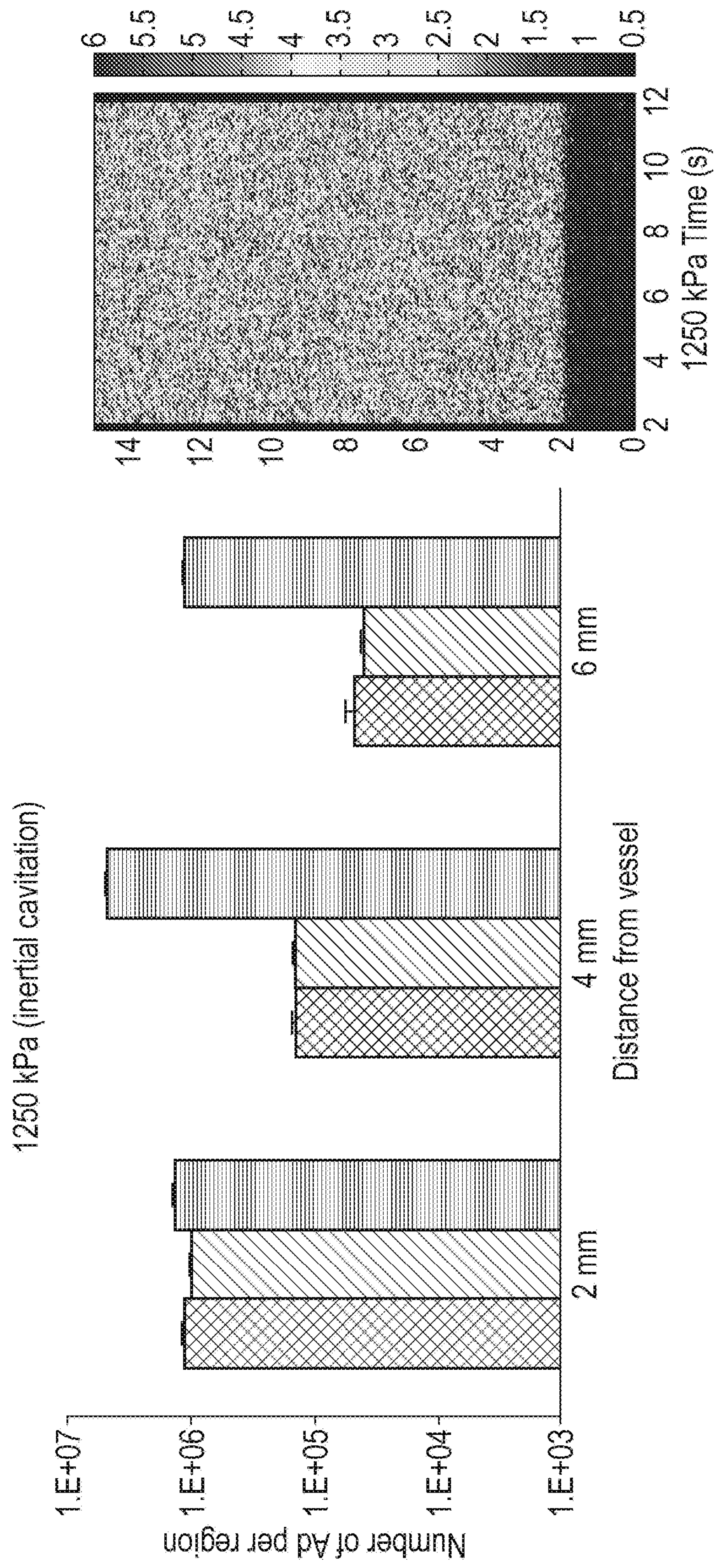
Figure 3G:
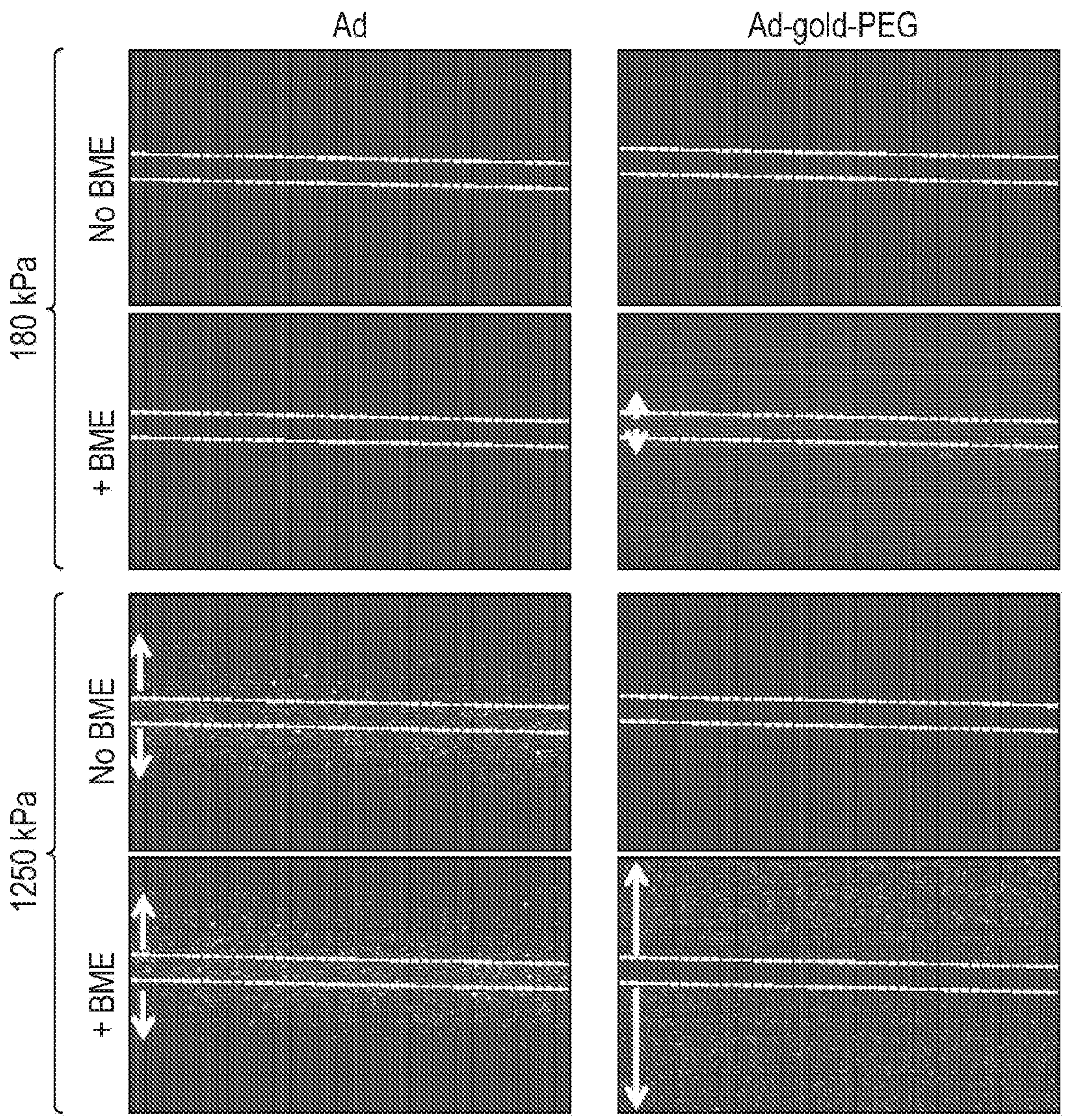

Results from ζ-potential (FIG. 1*b*) demonstrated that the gold was coated successfully in the PEG dandelions since ζ-potentials became less positive as amine groups on the gold were removed by reaction with PEG, changing from 2.6 to 1.5 mV upon the addition of 5 kDa PEG and 0.2 mV after subsequent addition of 2 kDa PEG. FIG. 3*c* demonstrates that the dandelions were successfully attached to the Ad as the ζ-potential of Ad increased from −16.9 to −13.9 mV upon reaction with gold-PEG.

Gold-PEG had a greater hydrodynamic diameter (15 nm) than gold, which measured 6.3 nm. Unmodified Ad measured 117 nm, whereas Ad–gold-PEG measured 149 nm, a 32-nm increase which corresponds to the combined size of two gold-PEG dandelions, demonstrating a good gold-PEG coating geometry.

Treatment of Ad–gold-PEG with reducing agent (beta-mercaptoethanol) cleaved the 5 kDa PEG and returned Ad to its original size.

Figure 1D:
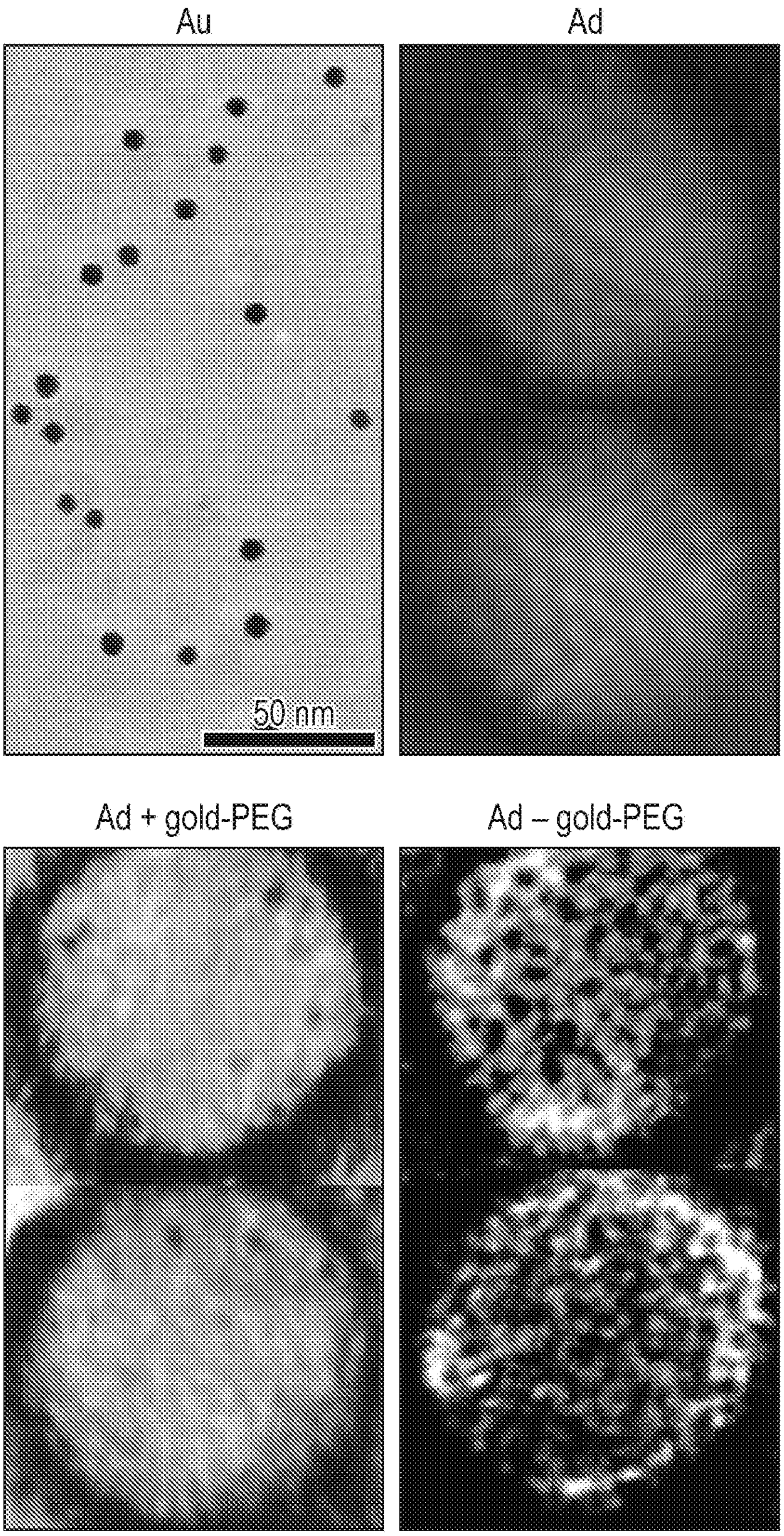
FIG. 1*d* shows transmission electron microscopy of gold-PEG, Ad, Ad+gold-PEG or Ad−gold-PEG constructs. The red scale bar represents 50 nm. For fixation, visualisation, and image capture, see on line materials and methods.

Alteration to Ad capsid protein composition and size after stealthing with gold-PEG was characterized by separating the capsid proteins on a polyacrylamide gel. The resulting SDS-PAGE silver stain (FIG. 1*d*) indicated that neither Ad (lanes 1 and 2) nor non-linked Ad+gold-PEG (lanes 5 and 6) showed a difference in Ad capsid polypeptide band intensity in the presence or absence of the reducing buffer BME. In contrast, analysis of conjugated Ad–gold-PEG (lanes 3 and 4) showed a dramatically different band migration pattern depending on the presence or absence of reducing buffer. Notably, in the absence of reducing agent (lane 4) there was little discernible migration of Ad capsid protein into the gel, indicating that most Ad capsid protein was bound to gold-PEG and unable to properly penetrate the polyacrylamide. No bands were evident for Ad polypeptides II, III, and IV; notably the bands which did stain in lane 4 corresponded to internal capsid proteins such as VI and VII. However, upon exposure to reducing buffer 9 (lane 3), Ad–gold-PEG showed equivalent protein migration and intensity to that of Ad and non-linked Ad+gold-PEG, signifying the reduction-induced breakage of disulfide bonds between Ad and gold-PEG to un-stealth Ad to its original form. TEM images (FIG. 1*e*) showed 60 gold-PEG linked per Ad capsid. Notably, because the 12 trimeric fibre proteins are lost from Ad during TEM processing the gold-PEG attached to these regions cannot be visualised by this method. However, as SDSPAGE demonstrated that sufficient gold-PEG was attached to the trimeric fibre proteins to prevent its migration it is reasonable to calculate that at least 3 gold-PEG were attached per fibre. Adding the capsid (60) and fibre values (36) gives a total of approximately 96 gold-PEG per Ad. TNBS analysis showed the loss of 111 amine groups from Ad upon reaction with gold-PEG. These analyses therefore prove that this stealthing procedure enables the overwhelming majority of each of 96 gold-PEG to be linked to Ad by just one bridging 5 kDa PEG molecule.

Reference Example 1

Passive Targeting of Ad-Gold-PEG to Tumors

Figure 5A:
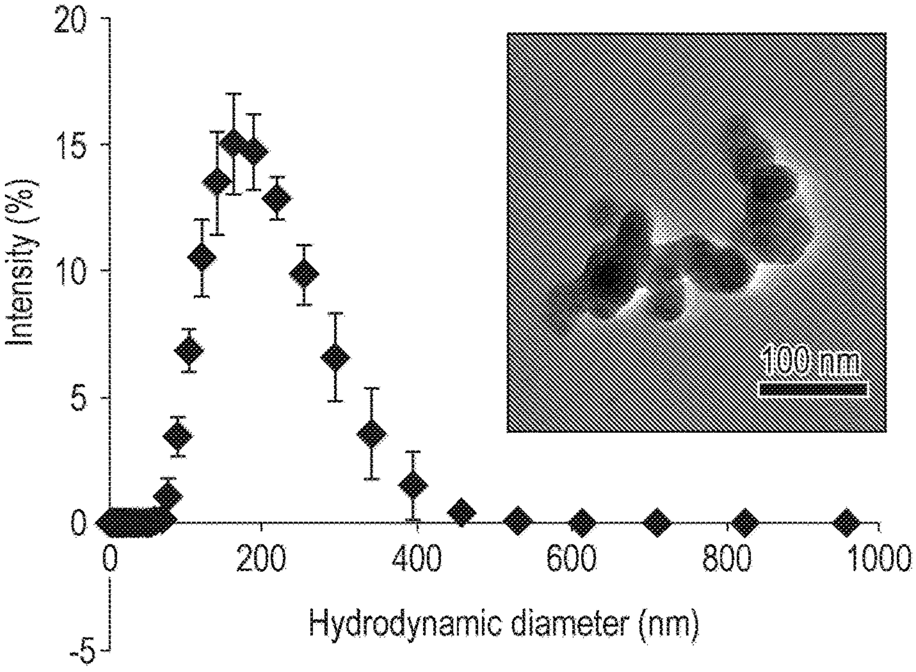
FIGS. 5*a* and 5*b* show hydrodynamic diameter and peak rarefactional focal pressure versus acoustic emission for carbon agglomerate nanoparticles.

In vivo studies were performed in tumor-bearing murine models. After i.v. injection of Ad, Ad-PEG, Ad-PHPMA or Ad–gold-PEG, blood samples were taken at 5, 15, and 30 min, and tumour and liver samples were extracted following cull at 35 min. Blood circulation profiles of Ad, Ad-PEG, Ad-PHPMA and Ad–gold-PEG are shown in FIG. 5.

The control Ad, Ad-PEG and Ad-PHPMA circulation data was comparable to previous published results. The half-life of Ad–gold-PEG was more than 30 min, meaning it outperformed all other groups, including Ad-PHPMA. This indicates that the superior stealthing achieved with Ad-gold-PEG, as demonstrated in vitro by ELISA, impacted directly on circulation and hepatic capture in vivo. Crucially, TNBS analysis had shown improved stealthing with Ad–gold-PEG was achieved with modification of just 111 capsid amine groups compared to 1332 with Ad-PHPMA or 1007 with Ad-PEG.

Figure 2A:
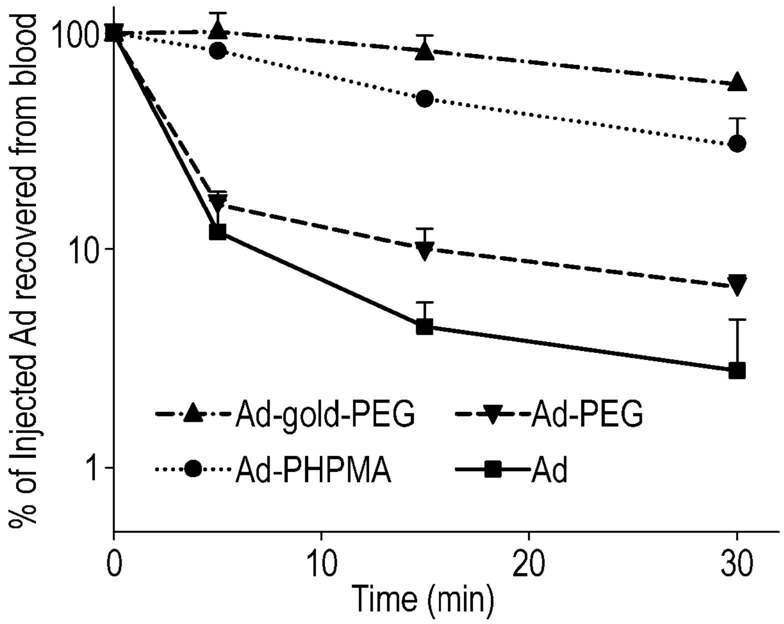
FIG. 2*a* shows blood sampling and quantification by QPCR. n=4, S.D shown. Ad−gold-PEG, different from all other groups.
Figure 2B:
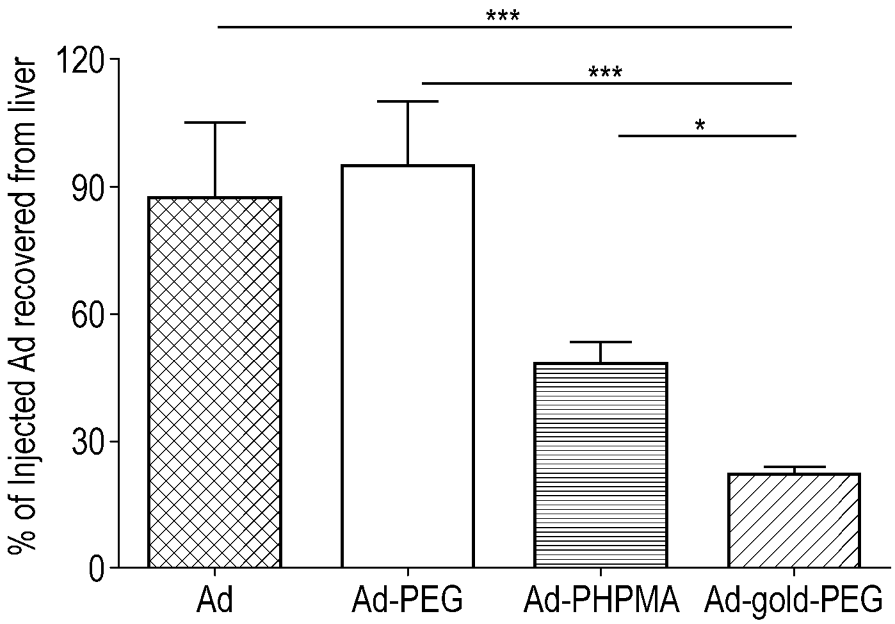
FIG. 2*b* shows total percentage of the injected dose accumulated in livers.
Figure 2C:
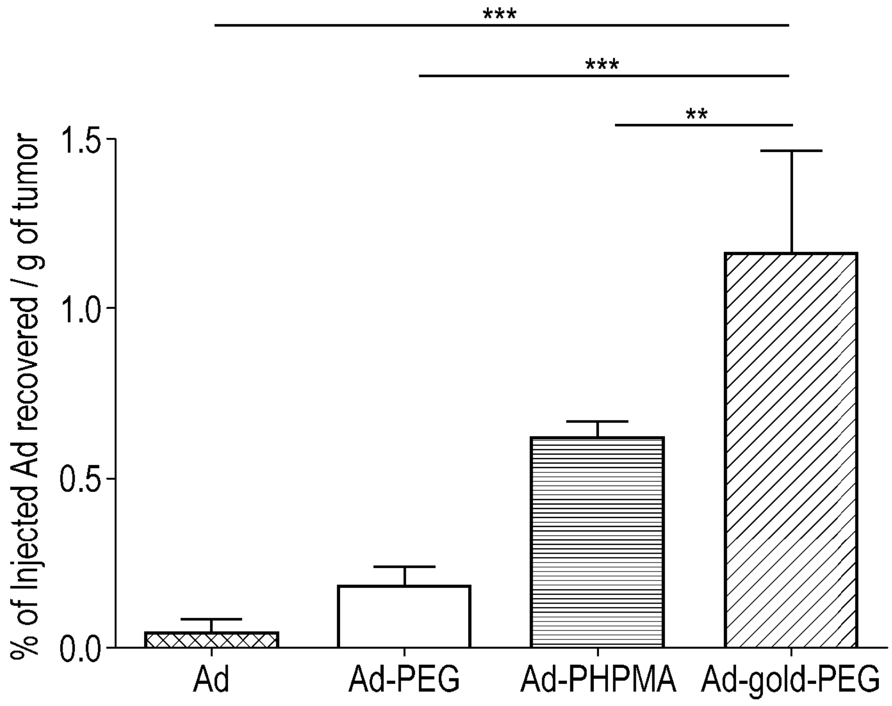
FIG. 2*c* shows total percentage of dose accumulated per gram of tumour mass. Each group had four mice (n=4), standard deviation shown. Groups compared using ANOVA followed by Newman-Keuls test for pairwise comparison of sub-groups; * and *** represents p-value<0.05 and 0.001, respectively.
Figure 2D:
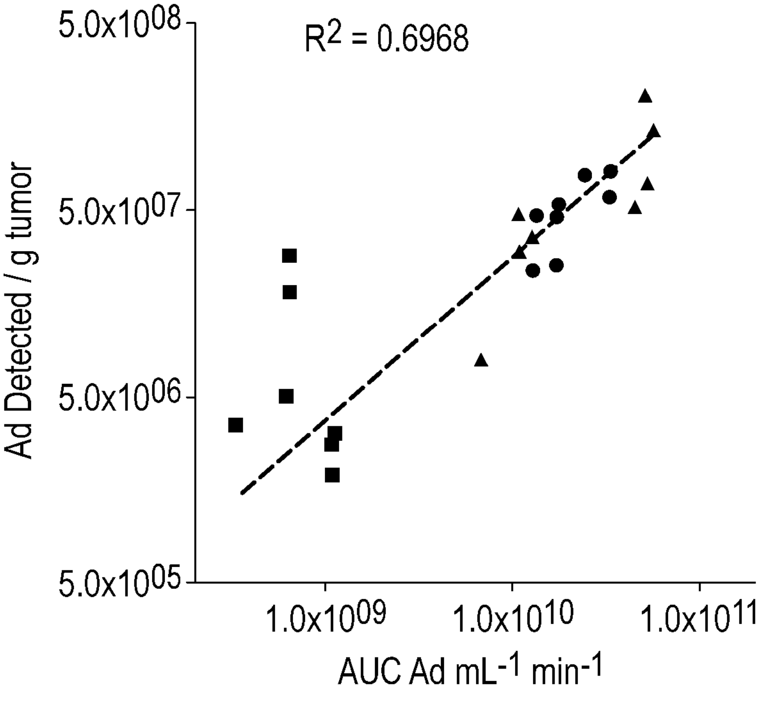
FIG. 2*d* shows the relationship between Ad plasma circulation profile and tumor accumulation. Each point represents one mouse treated with Ad (black square), Ad-PEG (white triangle), Ad-PHPMA (purple circle), and Ad-gold-PEG (blue triangle). Area under curve calculated from circulation data at 30 min time point for all mice, N=8. Correlation between AUC and Ad tumor accumulation (R=0.6968).

Bio-distribution of Ad, Ad-PEG, Ad-PHPMA, and Ad-gold-PEG is represented in FIG. 2*b* (liver capture) and FIG. 5*c* (tumor accumulation). More than 90% of Ad and Ad-PEG was captured by the liver. In contrast liver capture of Ad-PHPMA and Ad–gold-PEG decreased to 48% and 21%, respectively. Furthermore, 9-fold more Ad–gold-PEG than Ad particles were recovered from the tumor. Integration of the areas under the curve (AUC) for each sample in FIG. 2*c* and plotting of these data with their respective total Ad accumulated per gram of tumor, produced a strong correlation (FIG. 2*d*) with $R^2$=0.6968, indicating that passive tumor targeting of Ad is dependent on its plasma AUC. This demonstrates that the enhanced chemical coating and protection of Ad–gold-PEG leads to lower liver capture and extended circulation and ultimately EPR assisted increases in passive tumor accumulation.

Example 1

Active Targeting of Ad–Gold-PEG Using Focussed Ultrasound In Vitro

Experiments were performed to test if the presence of gold-PEG could increase Ad response to focussed ultrasound and consequently provide improved active delivery to tumors.

Increasing the density of a nanomedicine such as Ad by its attachment to gold-PEG increased its response to ultrasound induced cavitation events (FIG. 3) when co-injected with cavitation-inducing microbubbles (SonoVue).

The theoretical increase in density in going from Ad (1.37 g/mL) to Ad–gold-PEG (3.35 g/mL) was confirmed by dramatically different ultra-centrifugation separation on caesium chloride gradients of Ad, Ad-PHPMA and Ad–gold-PEG (FIG. 3*a*). 99% of Ad–gold-PEG being recovered from the bottom of the tube.

When applied through a flow channel in a tissue mimicking material (TMM) and exposed to ultrasound the amount of movement into the TMM (as measured by QPCR for Ad genomes) scaled with the amount of ultrasound induced inertial cavitation events (as measured by passive cavitation detection.

Modulating density altered response to ultrasound and provided precise control over the depth of penetration, which has important implications for the delivery of nanomedicines to tumors as well as transdermally in vaccination procedures. Significantly more Ad–gold-PEG, than Ad or Ad-PHPMA was moved into the TMM at all penetration depths tested. At the maximum pressure tested (1250 kPa), between 50 and 100-fold more Ad–gold-PEG was recovered at distances of 4 and 6 mm from the flow channel. Exposure to BME and analysis of the cells within the TMM for GFP transgene expression at 24 hours confirmed the Ad–gold-PEG to have maintained infection capacity and to have journeyed further than the Ad, whilst also demonstrating that the ultrasound parameters caused no intrinsic cell damage. When quantified using imageJ software significant increase ($p<0.001$) in the depth of infection was observed. Notably, in contrast to Ad, infection was only evident with Ad–gold-PEG when reducing agent BME was used suggesting enhanced selectivity for the tumor environment and therefore safety.

Example 2

Passive and Active Targeting of Ad-Gold-PEG In Vivo

Experiments were performed to test whether the enhanced passive targeting of Ad, achieved as a result of improved stealthing with gold-PEG, could be combined with the increased ultrasound-mediated active targeting, achieved as a result of the increased density provided by stealthing with gold-PEG.

Figure 4A:
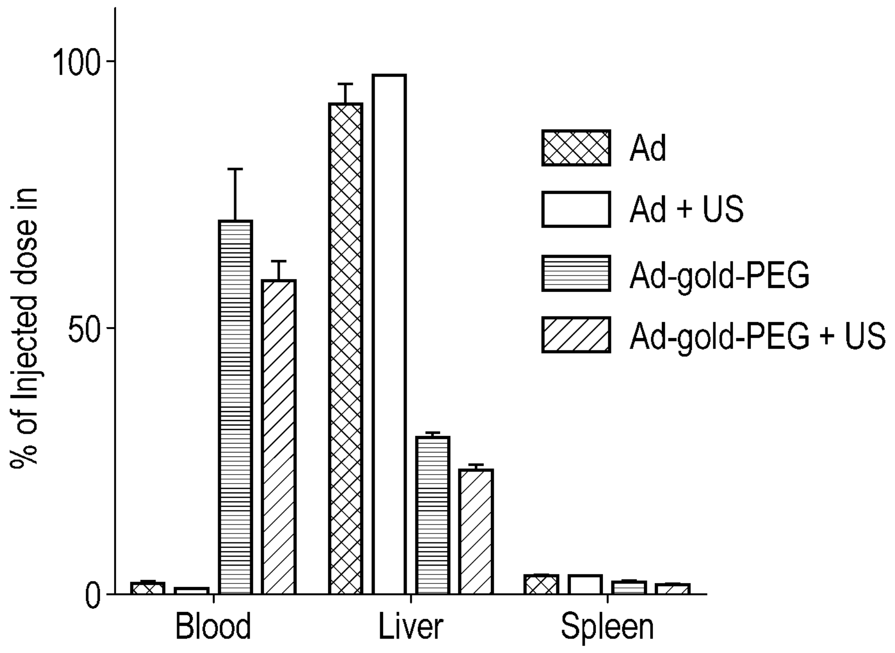
FIGS. 4*a* and 4*b* show the influence of ultrasound on active targeting to tumors.
Figure 4B:
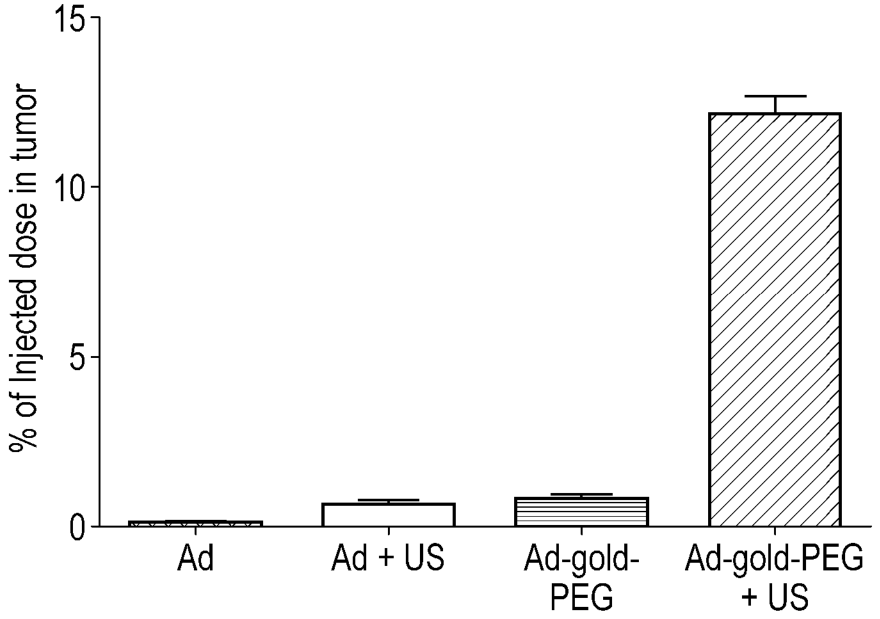

When cancer cell killing oncolytic adenovirus was modified with gold-PEG and delivered to pre-clinical models, in accordance with FIG. 2*a*, substantially reduced liver capture (29.3%, SD 2.14 vs 91.6% SD 8.36) was obtained, resulting in 35-fold increase in the circulating dose at 30 min (FIG. 4*a*). This again provided a significant ($p<0.005$) increase in tumor load of Ad–gold-PEG vs Ad, via passive targeting (0.84% vs 0.12%). When ultrasound was added as a stimulus for active targeting of Ad–gold-PEG a significant ($p<0.001$) and substantial (14-fold) increase in its tumor accumulation was observed (12.2%, SD 0.97). The increased tumor uptake was even evidenced by a decrease in the amount of dose captured by the liver (23%, SD 1.8).

The combined benefit of improved passive targeting, achieved by enhancing stealthing, and improved ultrasound-mediated active targeting, by enhancing particle density, provided 100-fold more Ad–gold-PEG within ultrasound treated tumors than Ad in non-ultrasound treated tumors.

Preparation Example 2

Cavitation-Initiating Carbon Agglomerates

Figure 5B:
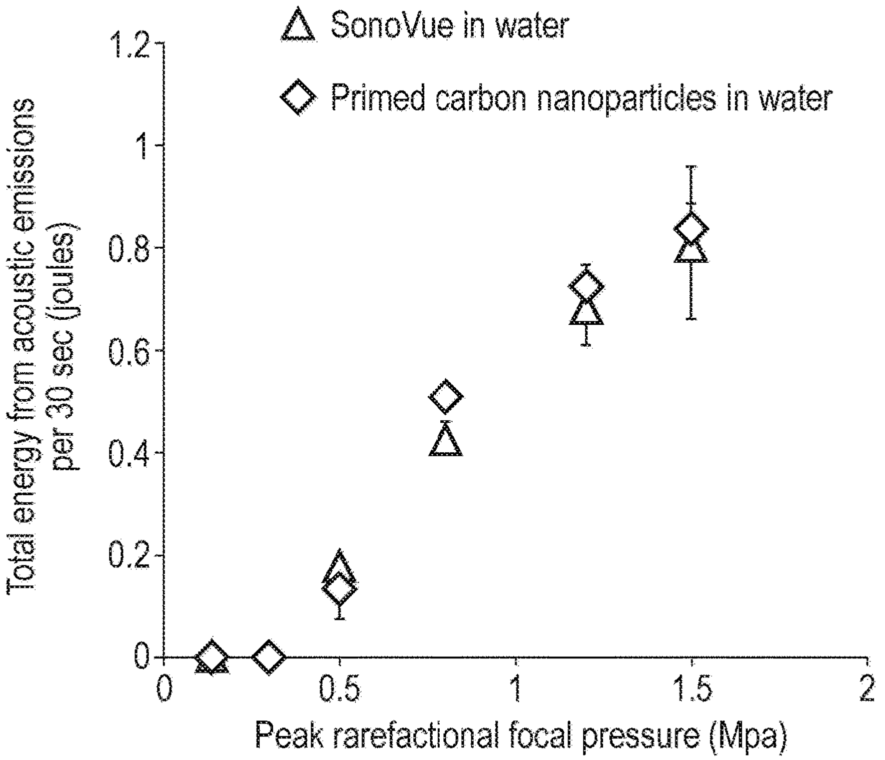

Cavitation-inducing carbon agglomerate nanoparticles of size<400 nm (FIG. 5*a*) were produced according to the following protocol:

1. Prepare 0.2 mg/ml carbon (7 mg mesoporous carbon+35 ml filtered DI water)
2. Shake vigorously for 10 seconds
3. Sonicate with probe at approx 15 W for 5×30 seconds, shaking for 1 minute between sonications 4. Pipette contents into a fresh centrifuge tube
5. Centrifuge for 5 mins at 2000 g (acc=dec=9)
6. Pipette contents into a fresh centrifuge tube leaving approximately 10 ml
7. Centrifuge for 1 hour at 2000 g (acc=dec=9)
8. Pipette contents into a fresh centrifuge tube leaving approximately 10 ml
9. Shake for 10 seconds then leave for 10 minutes before testing for sonosensitivity The carbon agglomerates produced were shown to be capable of generating inertial cavitation at the nanoscale. Cavitation energy generated by the micron-sized agent SonoVue (FIG. 5*b*—blue triangles) and carbon agglomerates (FIG. 5*b*—red diamonds). In previous in vivo studies Ad, measuring 120 nm, was co-administered with SonoVue, measuring 2.5 μm, to provide the nuclei for the initiation of the cavitation events that drive Ad movement. Carbon nanoparticles (mean size 180 nm) can provide the same level of cavitation energy, but provide better Ad co-localisation, particularly in the perivascular space.

The invention claimed is:

1. A method of diagnosis or treatment of a human or animal subject, which method comprises administering to said subject an effective amount of an agent, wherein the agent comprises a therapeutic or diagnostic component which is covalently bound to a dense component, the dense component having a density greater than that of the therapeutic or diagnostic component, wherein the method comprises administering to the subject a further agent which is a cavitation initiator, said cavitation initiator being a substance comprising one or more gas or vapor filled cavities or bubbles, and wherein the method further comprises exposing the subject to ultrasound, wherein the cavitation initiator undergoes inertial cavitation in the subject.

2. A method according to claim 1, wherein the dense component has a density which is two times or more that of the therapeutic or diagnostic component.

3. A method according to claim 1, wherein the agent has a density of 1.5 g/mL or more.

4. A method according to claim 1, wherein the dense component is cleavably bound to the therapeutic or diagnostic component.

5. A method according to claim 4, wherein the dense component is bound to the therapeutic or diagnostic component with a polymer chain comprising a cleavable moiety.

6. A method according to claim 1, wherein the dense component comprises a nanoparticle from 1 to 1000 nm in size.

7. A method according to claim 6, wherein the dense component comprises a nanoparticle of a metal.

8. A method according to claim 7, wherein the metal is gold.

9. A method according to claim 6, wherein the nanoparticle has a plurality of polymer chains attached thereto.

10. A method according to claim 8, wherein the nanoparticle has a plurality of polymer chains attached thereto.

11. A method according to claim 1, wherein said cavitation initiator comprises an agglomerate of carbon nanoparticles.

12. A method according to claim 1, wherein the subject is exposed to ultrasound at an ultrasound pressure amplitude of less than 5 MPa.

13. A method according to claim 12, wherein the subject is exposed to ultrasound at an ultrasound pressure amplitude of 3 MPa or less.

14. A method according to claim 1, which is a method of treating a tumor in a patient in need thereof.

15. A method according to claim 1, wherein the agent has a size of from 100 to 500 nm.

16. A method according to claim 14, wherein the agent has a size of from 100 to 500 nm.

17. A method according to claim 1, wherein the subject is exposed to ultrasound at an ultrasound pressure of at least 0.5 MPa.

* * * * *